United States Patent [19]

Ochi et al.

[11] 4,012,587
[45] Mar. 15, 1977

[54] SOLID STATE IMAGE SENSOR

[75] Inventors: Shigeyuki Ochi, Machida; Seisuke Yamanaka, Mitaka; Yasuo Kanou, Tokyo, all of Japan

[73] Assignee: Sony Corporation, Tokyo, Japan

[22] Filed: Jan. 26, 1976

[21] Appl. No.: 652,116

[30] Foreign Application Priority Data

Jan. 30, 1975 Japan .................. 50-12740

[52] U.S. Cl. .................. 358/213; 357/24; 357/30; 250/211 J; 250/578; 307/221 D
[51] Int. Cl.[2] .................. H04N 3/16
[58] Field of Search ........... 357/24, 30; 250/211 J, 250/578; 307/221 D, 311; 178/7.1

[56] References Cited

UNITED STATES PATENTS

| | | | |
|---|---|---|---|
| 3,869,572 | 3/1975 | Carter | 178/7.1 |
| 3,896,474 | 7/1975 | Amelio et al. | 178/7.1 X |
| 3,940,602 | 2/1976 | Lagnado et al. | 178/7.1 X |

*Primary Examiner*—Robert L. Griffin
*Assistant Examiner*—Aristotelis M. Psitos
*Attorney, Agent, or Firm*—Hill, Gross, Simpson, Van Santen, Steadman, Chiara & Simpson

[57] ABSTRACT

In a solid state image sensor of the type which employs an inter-line transfer charge-coupled imaging device, the electrodes of the vertical shift registers are enlarged to extend to places which lie between image pick-up portions aligned in the vertical direction of the device. Each of the image pick-up portions comprises an image sensing area and a transfer gate. Preferably, every other image pick-up portion of a conventional CCD imaging device is removed to provide spacing between the image pick-up portions relative to the vertical direction.

10 Claims, 13 Drawing Figures

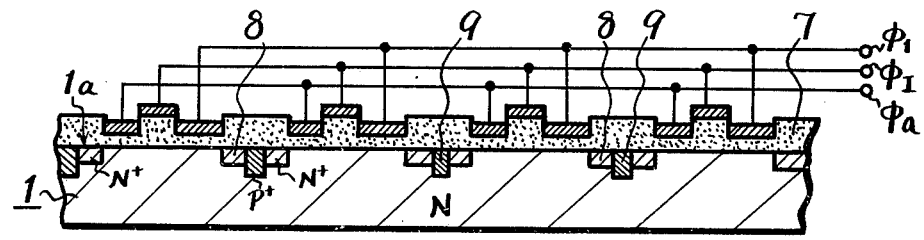
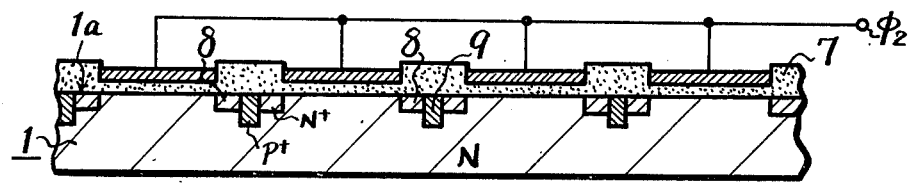
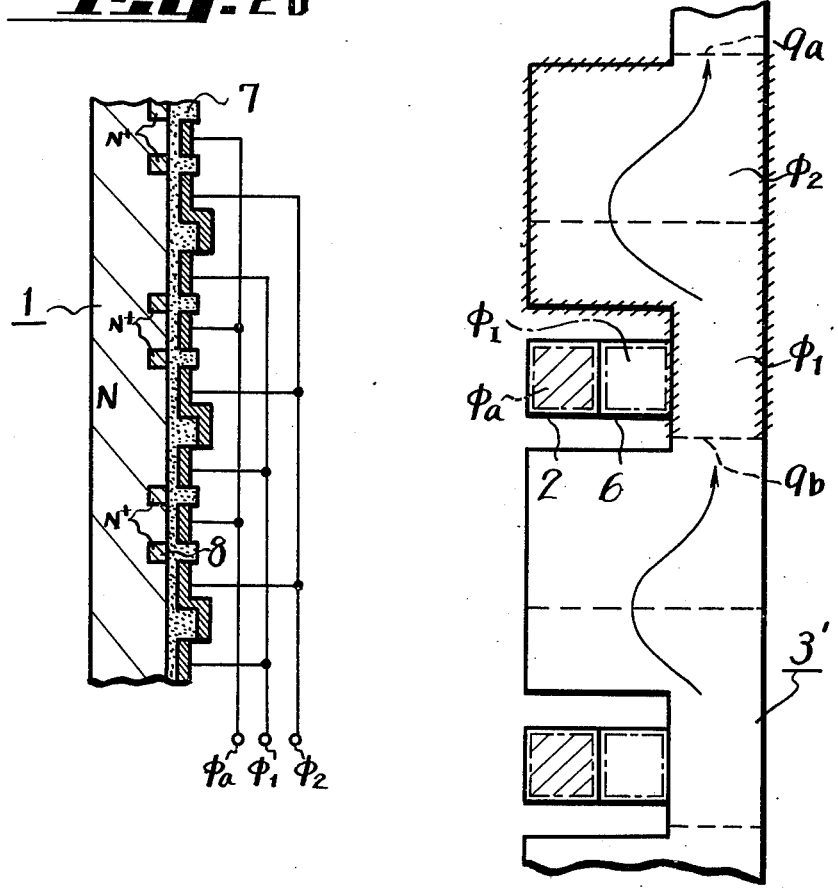

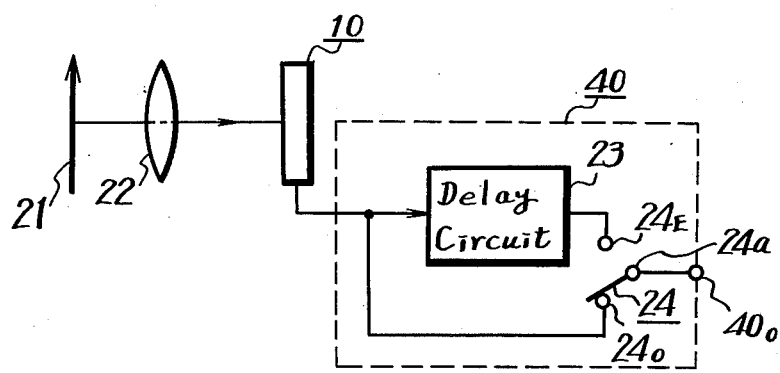
Fig-4
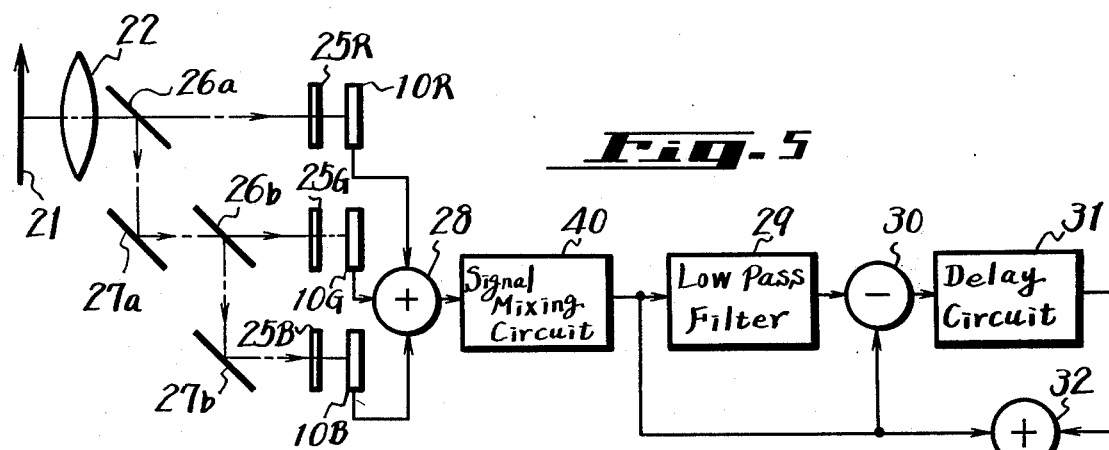
Fig-5
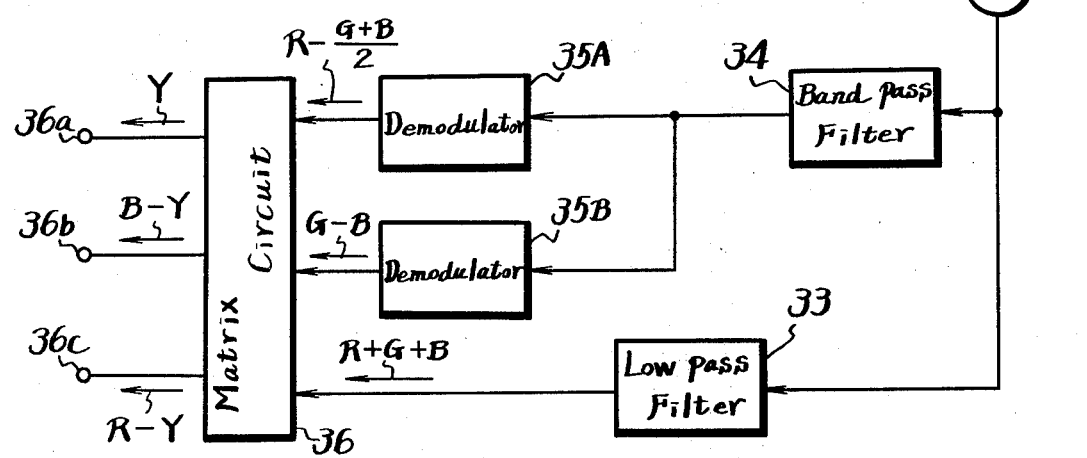

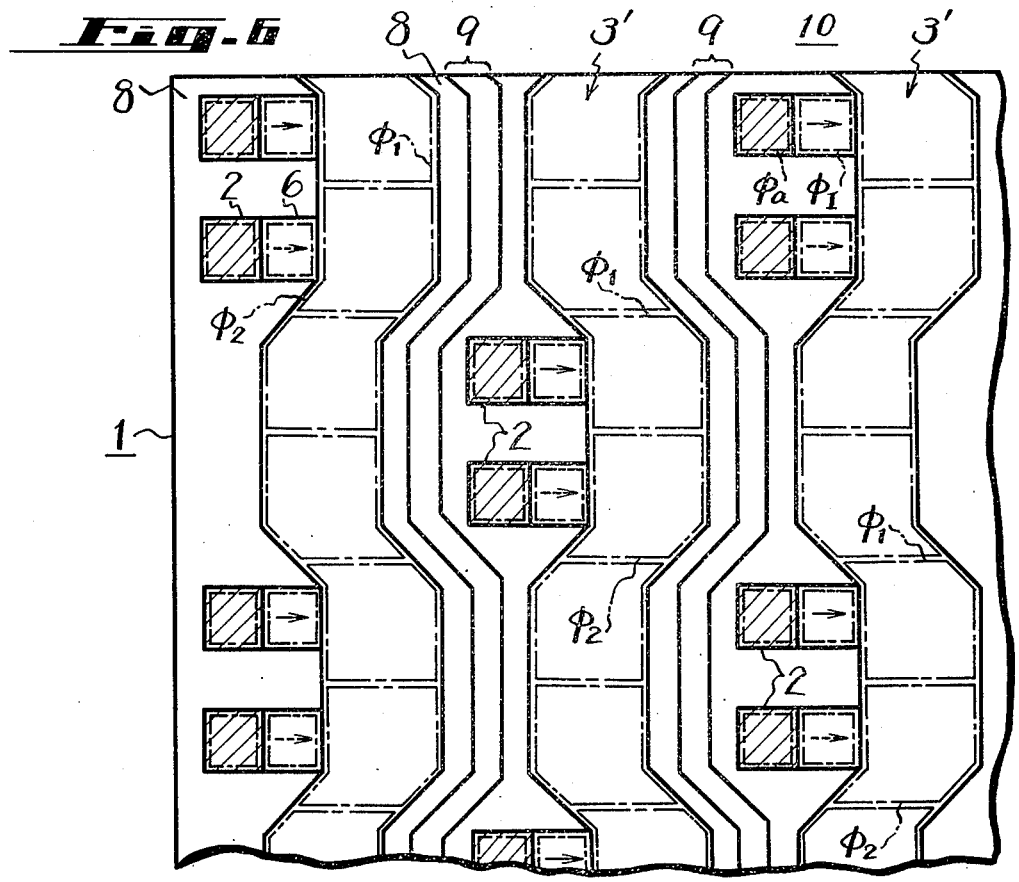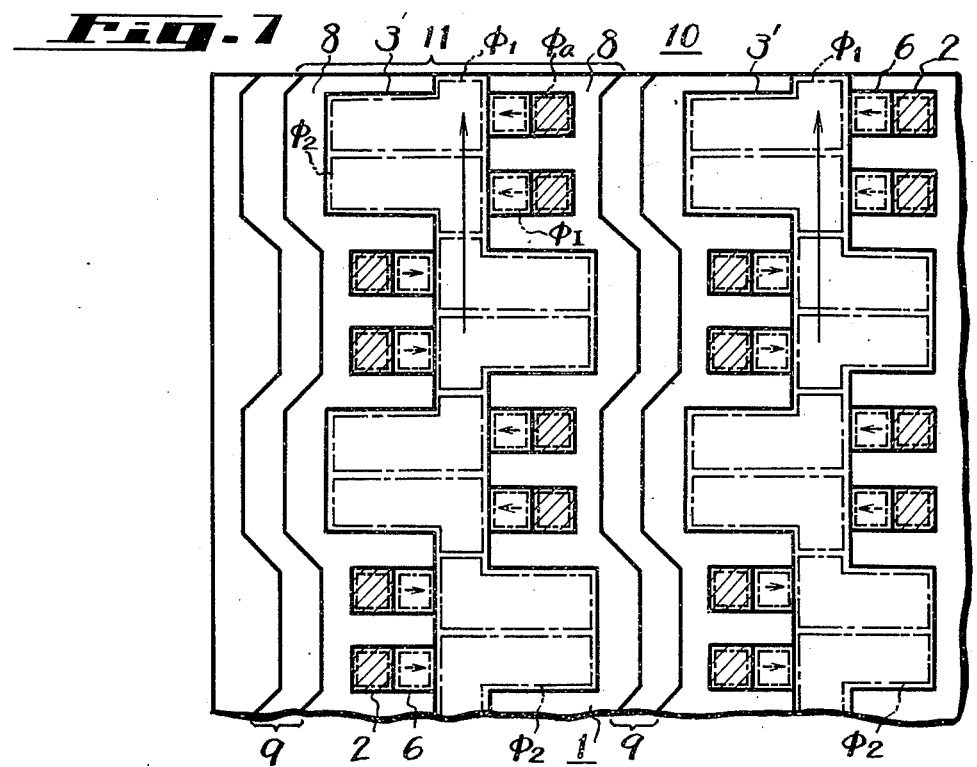

SOLID STATE IMAGE SENSOR

BACKGROUND OF THE INVENTION

1. Field of the Invention

This invention relates generally to a solid state image sensor, and is directed more particularly to a charge coupled image sensor of the inter-line transfer type.

2. Description of the Prior Art

In the art it is known to employ a solid state image sensor comprising, for example, a charge coupled device or element (CCD) arranged as an interline transfer system.

FIG. 1 shows a typical charge coupled device 10 of the prior art, which consists of a common semiconductor substrate 1. A number of sensing areas 2 are formed on the semiconductor substrate 1 and aligned as picture elements covering a two-dimensional matrix or area. Vertical shift register 3 is provided adjacent each vertical column of sensing areas 2 in the horizontal scanning direction. Each of the vertical shift registers extend in a vertical direction. A horizontal shift register 4 is provided for transferring the stored carriers to an output terminal.

In order to obtain an output signal from the solid state image sensor 10, minority carriers stored in each sensing area 2 in response to light information are transferred during the vertical blanking interval of a television signal at every vertical line to the vertical shift register 3 (parallel transfer). Secondly, the carriers are transferred through each vertical shift register 3 in the vertical direction (serial transfer) sequentially. Finally, the carriers are read out through the horizontal shift register 4 at every horizontal scanning line. Thus, a desired output signal can be obtained at the output terminal (not shown) of the horizontal shift register 4.

Since the transfer of stored carriers is carried out at every horizontal scanning line, this transfer system is generally called an interline transfer (or interline) shift system.

The arrows appearing in FIG. 1 show the direction of the carrier transfer. When an interlace scanning system is employed during image picking up, the dotted line arrows in FIG. 1 show carrier transfers in the even fields. Thus, the stored carriers are transferred to the vertical shift registers 3 only through the paths shown by solid line arrows in the odd fields.

To obtain sufficient resolution with the above prior art solid stage image sensor 10, it becomes necessary to increase the number of picture elements and hence it becomes very difficult to form a solid state image sensor on the semiconductor substrate 1 of predetermined dimensions without serious flaws developing.

Furthermore, the carrier transfer efficiency of the vertical shift registers of the prior art solid state image sensor is poor. Therefore, it has been difficult to form a practical solid state image sensor.

SUMMARY OF THE INVENTION

According to an aspect of this invention, there is provided a solid state image sensor employing a charge transfer device which comprises a plurality of image pickup portions aligned in two dimensional areas of a semiconductor body, each having an image sensing area and a transfer gate area. A plurality of vertical shift registers extend adjacent the image pickup portions in the vertical direction. Each of the vertical shift registers has plural sets of electrodes which are enlarged to extend between the vertically arranged image pickup portions.

A horizontal register is provided for receiving collected light information from the plurality of parallel vertical shift registers and for supplying the light information in serial form to an output.

Accordingly, it is an object of this invention to provide a solid state image sensor in the form of an interline shift system in which the carrier transfer efficiency can be greatly improved as compared with prior art systems by increasing the area of an electrode at the vertical shift register without introducing any deterioration in the vertical resolution.

It is another object of the invention to provide a solid state image sensor in which picture elements aligned in the vertical direction are formed at every horizontal scanning period (1H) and unused areas of the picture elements are effectively utilized to achieve the above object.

It is a further object of the invention to provide a solid state image sensor in which vertical shift registers are arranged in a zig-zag manner to increase the area of a transfer electrode and hence to increase a charge transfer efficiency.

It is a still further object of the invention to provide a solid state image sensor in which information corresponding to two columns are handled by one vertical shift register, so that the number of vertical shift registers can be reduced by one-half and accordingly, spare areas remain.

The other objects, features and advantages of the invention will become apparent from the following description taken in conjunction with the accompanying drawings in which same reference numerals designate the same elements.

BRIEF DESCRIPTION OF THE DRAWINGS

FIGS. 2B, 2C and 2D are sectional views taken along lines IIB—IIB, IIC—IIC and IID—IID on FIG. 2A, respectively;

FIG. 3 is an enlarged view of a portion of FIG. 2A used for explaining the invention;

FIG. 4 is a schematic diagram showing one of the embodiments where the image sensor of the invention shown in FIG. 2A is used as a television camera apparatus;

FIG. 5 is a schematic diagram showing one of the embodiments where the image sensor of FIG. 2A is used as a television color camera apparatus;

FIGS. 6, 7 and 8 are top views of other embodiments of the solid state image sensors of the invention.

DESCRIPTION OF THE PREFERRED EMBODIMENTS

An example of the solid state image sensors according to the present invention will be hereinbelow described with reference to the drawings.

Figure 1:
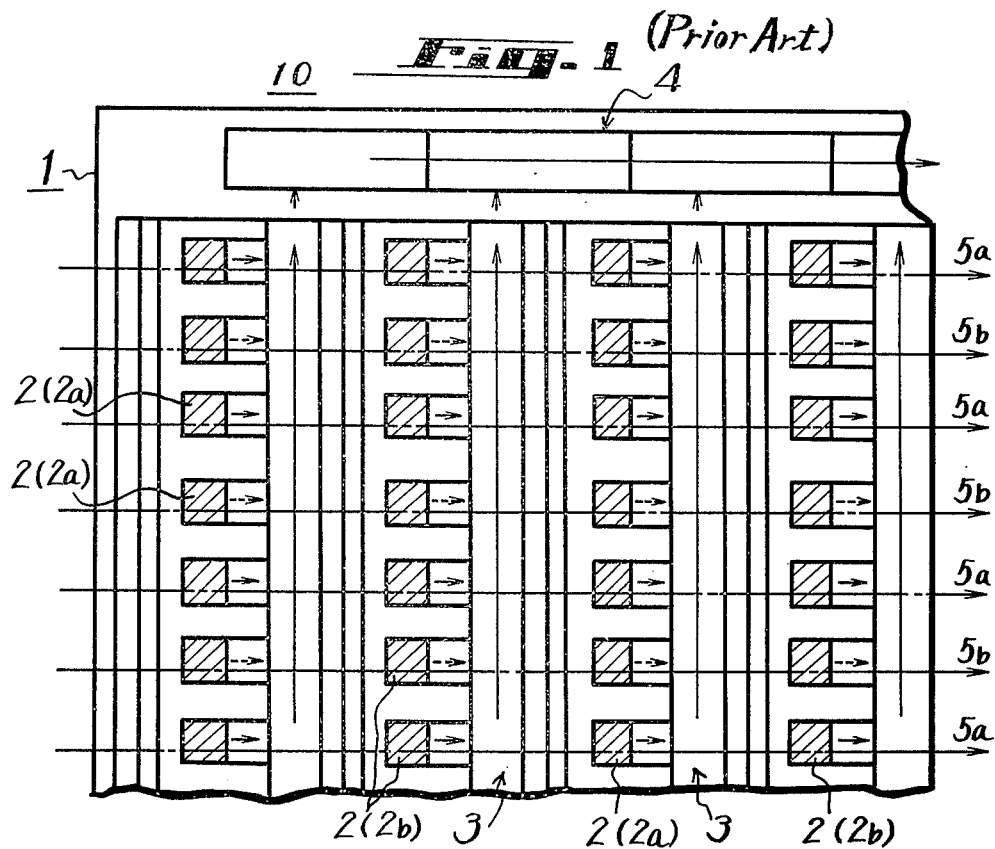
FIG. 1 is a plan view showing an example of the prior art solid state image sensor of the interline transfer type using a charge coupled device.

For better understanding of the present invention, reference is made to FIG. 1 in which the picture elements of odd numbered columns with respect to the horizontal scanning direction will be referred to as 2a, and the picture elements of even numbered columns with respect to the horizontal scanning direction will be referred to as 2b, respectively. Furthermore, in FIG. 1, the odd numbered horizontal scanning lines will be referred to as 5a and the even numbered horizontal scanning lines will be referred to as 5b, respectively.

Figure 2A:
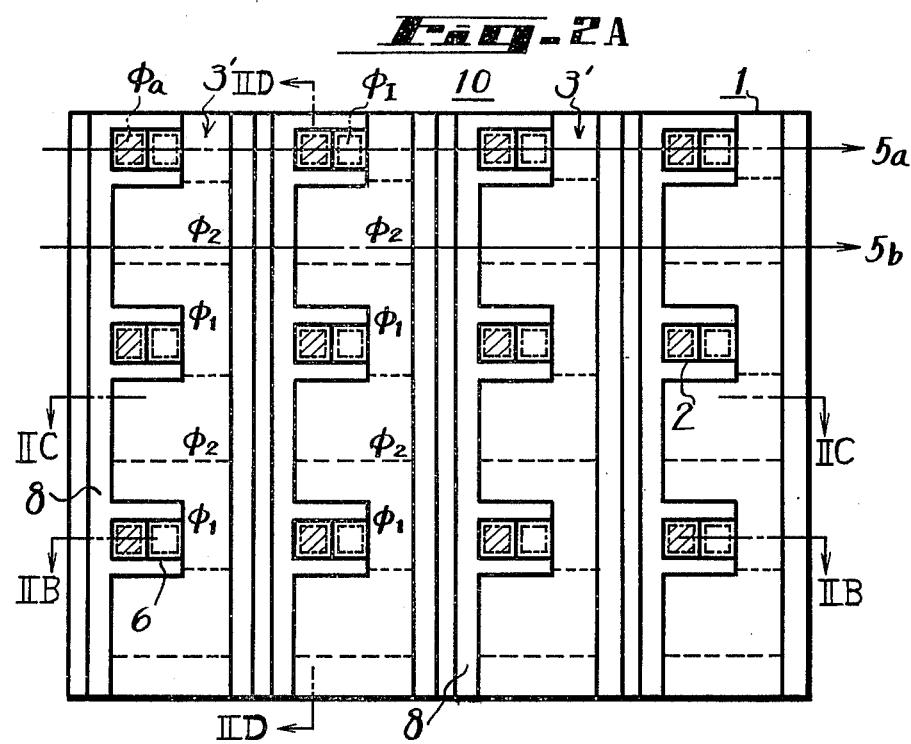
FIG. 2A is a top view of an embodiment of the solid state image sensor according to this invention.

In FIG. 2A which shows one embodiment of this invention, reference numeral 10 generally designates a main portion of one embodiment of the solid state image sensor according to the invention. As mentioned previously, the horizontal scan line picture elements are arranged on every other line as compared with the arrangement of the prior art device shown in FIG. 1.

In the example of FIG. 2A, the picture elements on the even numbered horizontal scanning lines 5b are omitted. The planned construction is the same as shown in the figure.

In FIG. 2A, areas shown by dot-dash lines are areas for storing and transferring carriers which will be hereinbelow called image sensing or pick up portions. In FIG. 2A, $\phi_a$ designates electrodes for storing carriers and $\phi_1$ gate electrodes which are provided on gate regions 6 for shifting the stored carriers to vertical shift registers 3', respectively. Since FIG. 2A shows an embodiment in which the carriers are transferred according to a two-phase clock, each of the vertical shift registers 3' is provided with a set of two electrodes $\phi_1$ and $\phi_2$. Hence, the total number of electrodes is greater than the number of picture elements in the vertical direction by two times.

With the invention, the electrode $\phi_1$ (or $\phi_2$) of the vertical shift register 3' is extended to the area where the picture elements are omitted to increase the area of the electrode. As a result, each shift register 3' is formed as a zig-zag pattern.

The cross-sectional views and longitudinal-sectional view of the solid state image sensor 10 constructed as above are shown in FIGS. 2B, 2C and 2D, respectively. In this example, a semiconductor substrate of an N-type conductivity is used as the semiconductor substrate 1, and the above mentioned plurality of electrodes are coated on an upper surface 1a of the semiconductor substrate 1 at desired positions through an insulating layer 7 made of, for example, silicon dioxide SiO$_2$. Since such a construction is a form of CCD (charge coupled device or element), the desired solid state image sensor 10 results. In the semiconductor substrate 1 there are formed regions 8 which serve as channel stoppers.

The conductivity type of an overflow drain region 9, which is formed in the region 8, differs from that of the substrate 1 and is a P+ type, for example. In the illustrated example, the region 9 is so formed that its width is much narrower than that of the region 8 of the channel stopper. Of course, it is possible that the width and shape or configuration of the region 9 can be selected in accordance with the dimension of the region 8.

Since the transfer of carriers in the solid state image sensor is deteriorated by the trapping due to the boundary level in the substrate 1, the transfer efficiency is generally improved by the fat zero, hereinafter defined, which is electrically or optically created, or caused by always supplying a small amount of bias charge to the vertical shift register 3'. Accordingly, if the area of the electrode of the vertical shift register 3' is expanded in association with the fat zero, the effect of the minority carrier trapping due to the boundary level can be further reduced and accordingly the transfer efficiency can be much improved.

For example, one of the standards for determining whether the transfer efficiency is high or low is the ratio of S and $l$ where S represents the area of the vertical shift register 3' and $l$ represents the length of one side (edge) which acts to trap carriers and which can not be covered by the fat zero. In this case, the length $l$ of the side which acts to trap carriers is the length of the side forming the boundary face which is not covered by the fat zero, in the boundary faces of a depletion layer caused by the electrode for the carrier transfer. When the direction of carrier transfer is selected as indicated by arrows in FIG. 3, boundary faces 9a and 9b, which are perpendicular to the carrier transfer direction indicated by the arrows, are covered by the fat zero. Therefore, the total lengths of the sides of the boundary faces other than the above boundary faces (which sides are shown with hatches in FIG. 3) become an important factor.

Accordingly, if the area S is greater than the length $l$ or the ratio S/$l$ is great, the influence of the trapping at the boundary face becomes small and, as a result the transfer efficiency can be improved. Therefore, it will be apparent that if the area of the electrode is expanded, as in this invention, the transfer efficiency can be effectively improved. Although practical values will be described later, it should be noted that the transfer efficiency is improved by about 20~50% as compared with the prior art.

As described previously, in the solid state image sensor 10 shown in FIG. 2A, the picture elements 2 corresponding to the horizontal scanning line at every other 1H are omitted. Thus, when a video output signal is derived by using this solid state image sensor 10, the image sensor 10 may be connected with circuitry of the type shown in FIG. 4.

In FIG. 4, reference numeral 21 designates an object to be picked up, 22 an optical lens system, 23 a delay circuit of 1H, 24 a switch which is changed over at every 1H, and 40 a signal mixing circuit. The switch 24 consists of a movable contact 24a which is connected to an output terminal 40$_O$ and fixed contacts 24$_O$ and 24$_E$. If the light information corresponding to the odd numbered horizontal scanning lines 5a is read out as an output signal, the switch 24 is changed over as shown in FIG. 4 or the movable contact 24a thereof contacts with its fixed contact 24$_O$. However, if the light information corresponding to the even numbered horizontal scanning lines 5b is read out, the information before 1H is delivered to the output terminal 40$_O$. In general, there is a vertical correlation, so that a reproduced picture is not deteriorated even if such a signal tratement is carried out.

An embodiment in which a color signal is treated by the solid state image sensor 10 will be described with reference to FIG. 5. In the color television camera apparatus shown in FIG. 5, three solid state image sensors 10R, 10G and 10B are used, each of which is the same as the image sensor 10 described above. Monochromatic filters 25R, 25G and 25B corresponding to R (red), G (green) and B (blue) are located in front of the solid state image sensors 10R, 10G and 10B, respectively. Thus, desired color separated images of the object 21 are picked up by the image sensors 10R, 10G and 10B, respectively. In FIG. 5, reference numerals 26a and 26b are partially transparent half mirrors, and 27a and 27b complete reflective mirrors.

The positional relations between the color separated images and the image sensors 10R to 10B are selected such that they are shifted by $\frac{1}{3}\tau_H$ (where $\tau_H$ represents the alignment pitch of picture elements in the horizontal scanning direction) in the horizontal direction with respect to one another. Therefore, the color separated images are projected with a phase difference of 120°. Video output signals are read out from the respective image sensors 10R to 10B sequentially and alternately, and then fed through an adding circuit 28 and the signal mixing circuit 40 (which is shown in FIG. 4) to a low pass filter 29 whose cut-off frequency is about 20 MHz. The low pass filter 29 is interposed so that the resolution in the vertical direction is not deteriorated in association with the structure later described. To this end low hand components which may affect the resolution are not altered.

The output signal from the filter 29 and the composite signal from the signal mixing circuit 40 (which is not limited in bandwidth) are supplied to a subtracting circuit 30 which delivers the high band component thereof. The output signal from the substracting circuit 30 is delayed by 1H through a delay circuit 31 and is then supplied to an adding circuit 32 which is supplied with the composite signal from the mixing circuit 40. Thus, the output signal from the adding circuit 32 contains the low band components which have not passed through the operational treating system. The output from adding circuit 32 is supplied to a low pass filter 33 whose cut-off frequency is 5.0 MHz. This low pass filter 33 produces a modulated (DC) component. The output signal from the adding circuit 32 is also supplied through a band pass filter 34 to demodulators 35A and 35B which have desired demodulation (detection) axes and demodulate color signal components, respectively. By way of example, the demodulator 35A demodulates the color signal component of $R - G + B/2$, while the demodulator 35B demodulates the color signal component of $G - B$, respectively, so that if these color signal components and the modulated component $R + G + B$ are supplied to a matrix circuit 36, the luminance signal Y and color difference signals $R - Y$ and $B - Y$ of, for example, the NTSC system, can be respectively obtained at output terminals 36a, 36b and 36c of the matrix circuit 36.

As described above, the image sensor 10 shown in FIG. 2A is used in the case where the interlace system is not employed for reception. A description of the interlace system is shown in FIG. 6, et seq. In such an embodiment, the picture elements on the adjacent horizontal scanning periods comprise sets, and such sets of picture elements are alternately located to form the solid state image sensor 10.

FIG. 6 shows a part of such an image sensor 10 enlarged in scale. In this case, the overflow drain region 9 is formed as a zig-zag pattern shown in FIG. 6.

In FIG. 7 an enlarged portion shows a further example of the image sensor 10. In this case, the picture elements are located alternately along both sides of the vertical shift register 3' and the light information from the picture elements at both sides of the vertical shift register 3' is transferred by one vertical shift register 3'. Thus, with the example of FIG. 7, the number of vertical shift registers 3' can be reduced without losing the effect of the invention previously described. Furthermore, the example shown in FIG. 7 has a simple construction and can be easily manufactured.

In the example of FIG. 7, an area 11 surrounded by the overflow drain regions 9 becomes a unit area in the horizontal scanning direction. One common vertical shift register 3' and two columns of picture elements are provided in the unit area 11.

Figure 8:
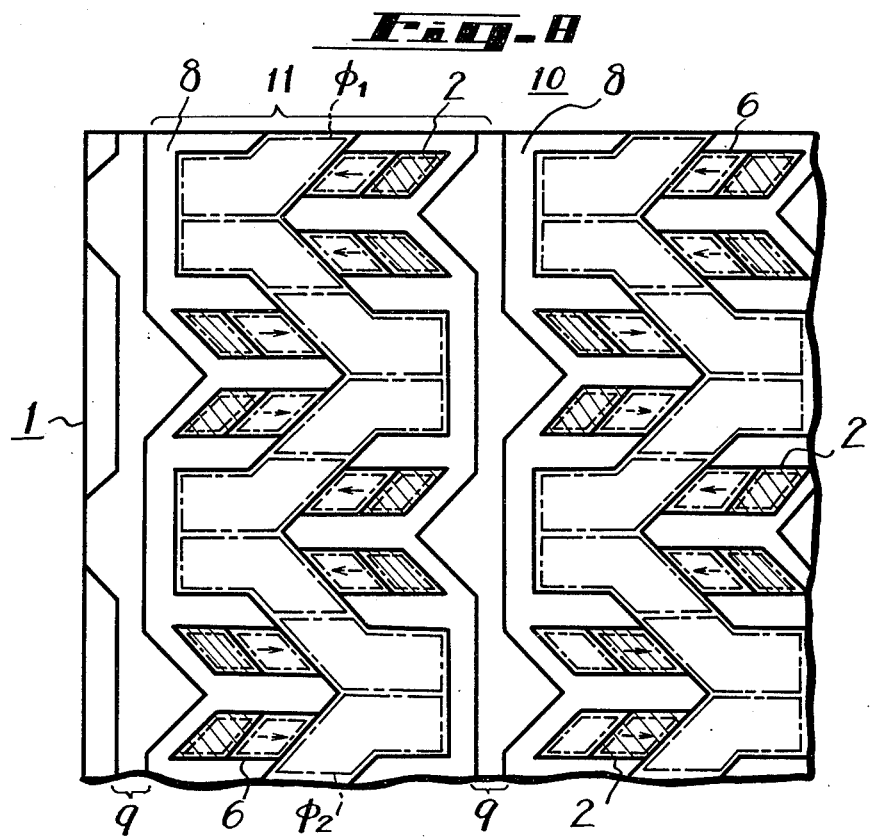

FIG. 8 shows a modification of the solid state image sensor 10 shown in FIG. 7.

As described above, with the present invention the picture elements at every other horizontal scanning period are omitted and the electrode of the shift register is expanded to the omitted area, so that the carrier transfer efficiency can be enhanced as compared with the prior art. With the solid state image sensors shown in FIGS. 2, 6 7 and 8, the carrier transfer efficiency can be improved by about 20~50% as compared with the prior art.

Figure 9A:
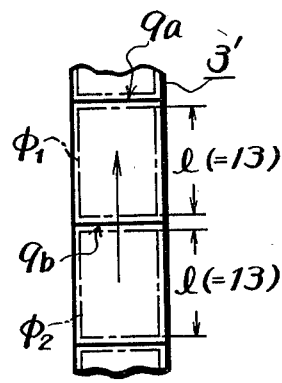
FIGS. 9A and 9B are schematic diagrams used for explaining operational effects of the invention.
Figure 9B:
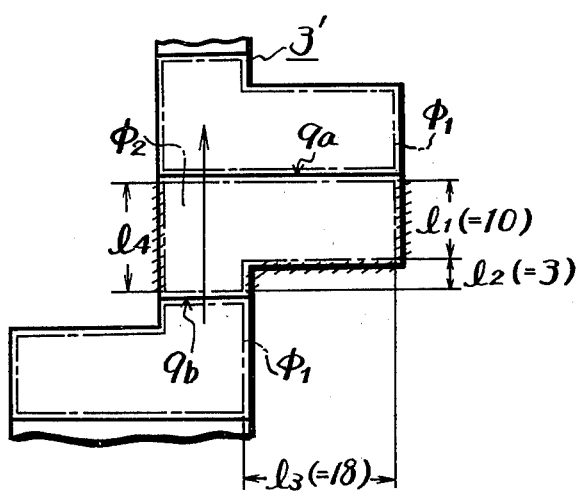

For better understanding, the comparison between the prior art shown in FIG. 1 and the present invention shown in FIG. 7 will be now described. With the example of the prior art shown in FIG. 9A, the ratio S/l is 4.5 (s/l = 4.5, but with one embodiment of the invention, $l = l_1 + l_2 + l_3 + l_4 = 44$ ($\mu$m) where S = 297 ($\mu$m) as shown in FIG. 9B, so that the ratio S/l becomes 6.8 (S/l = 6.8), which means that the carrier transfer efficiency is increased by about 50%.

Furthermore, when the electrode area is expanded, the number of carriers handled increases and noise is reduced.

As shown in FIGS. 7 and 8, if the picture elements are alternately located along both sides of each vertical shift register 3' with respect to the vertical direction, the number of vertical shift registers 3' can be reduced by ½ as compared with the number of picture elements theoretically required in the horizontal direction. Also, the number of horizontal picture elements can be reduced by ½ as compared with the prior art. In this case, if the signal is treated by utilization of a vertical correlation, the quality of reproduced pictures is hardly deteriorated. Furthermore, if a picture quality substantially the same as that of present state of the art television pictures is obtained, it is sufficient that the number of picture elements selected be only ⅔ that of the prior art with the number of vertical shift registers being selected in coordination with the number of picture elements. For example, if the number of picture elements in the horizontal direction is selected in the order of 280, sufficient resolution can be obtained. Thus, the number of vertical shift registers 3' in the solid state image sensor 10 is selected to be about 140.

As described in connection with FIGS. 7 and 8 of the present invention, the solid state image sensors can be easily manufactured.

The term "fat zero" as used herein means a constant bias charge injected to each well regardless of the magnitude of the transferring signal. See the article entitled "Two-Face Charge Coupled Device with Overlapping Polysilicon and Aluminum Gates," appearing in RCA Review, Volume 34 (1973), March, page 164.

It will be apparent to those skilled in the art that many modifications and variations may be effected without departing from the spirit and scope of the novel concepts of the present invention.

We claim as our invention:

1. A solid state image sensor employing charge transfer devices comprising:
   a. a plurality of image pickup portions aligned in two dimensions in areas of a semiconductor body, each image pickup portion having an image storing area and a transfer gate area;

b. a plurality of vertical shift registers extending adjacent said image pickup portions in the vertical direction, each vertical shift register having a plurality of electrode sets having enlarged portions which lie between said image pickup portions relative to the vertical direction; and c. a horizontal register for receiving collected light information from said plurality of vertical shift registers in parallel and for supplying the light information in a serial form to an output.

2. A solid state image sensor as claimed in claim 1, in which two of said image pickup portions aligned in the vertical direction form one group, and one of said electrode sets of each vertical shift register extends between the image pickup portions of each group.

3. A solid state image sensor as claimed in claim 2, in which said groups of image pickup portions are aligned in adjacent columns, said groups being vertically located to interleave.

4. A solid state image sensor as claimed in claim 1, in which the image pickup portions aligned in one vertical column and one vertical shift register form one vertical sensing arrangement, and an isolation area being formed between the adjacent vertical sensing arrangements.

5. A solid state image sensor as claimed in claim 2, in which the image pickup portions aligned in one vertical column and one vertical shift register form one vertical sensing arrangement, and an isolation area being formed between the adjacent vertical sensing arrangements.

6. A solid state image sensor as claimed in claim 3, in which the image pickup portions aligned in one vertical column and one vertical shift register form one vertical sensing arrangement, and an isolation area being formed between the adjacent vertical sensing arrangements.

7. A solid state image sensor adapted for using charge coupled transfer devices, comprising:

a. a semiconductor body;

b. image pickup means arranged in parallel columns on said semiconductor body;

c. vertical shift register means adjacent said columns of image pickup means, said vertical shift register means comprising a plurality of electrode sets, each electrode set comprising first and second electrodes which extend between at least some of the image pickup means in said columns; and d. horizontal register means on said semiconductor body for receiving collected light information from said vertical shift register means and for supplying said light information in serial form to an output.

8. An image sensor as claimed in claim 7, in which said image pickup means are grouped in pairs in each column, the pairs in adjacent columns being spaced to interleave, and said electrode sets extending between vertically adjacent pairs of said columns.

9. An image sensor as claimed in claim 7, in which one electrode set extends between each of the vertically adjacent image pickup means in said columns.

10. An image sensor as claimed in claim 7, in which said vertical shift register means have electrode sets which extend between interleaved pairs of pickup means on both sides of said vertical shift register means whereby a single vertical shift register means collects information from two columns of pickup means.

* * * * *